United States Patent [19]

Lukasavage et al.

[11] Patent Number: 5,212,308
[45] Date of Patent: May 18, 1993

[54] NONANE

[75] Inventors: William S. Lukasavage, Succasunna; Seymour Portnoy, Livingston; Jack Alster, Fair Lawn; Steven M. Nicolich, Saddlebrook, all of N.J.

[73] Assignee: The United States of America as represented by the Secretary of the Army, Washington, D.C.

[21] Appl. No.: 894,503

[22] Filed: Jun. 5, 1992

Related U.S. Application Data

[62] Division of Ser. No. 687,607, Apr. 15, 1991.

[51] Int. Cl.$^5$ ............................................ C07D 487/08
[52] U.S. Cl. ...................................................... 544/215
[58] Field of Search ......................................... 544/215

[56] References Cited

U.S. PATENT DOCUMENTS 3,979,379  9/1976  Siele ..................................... 544/215
4,048,167  9/1977  Paul et al. ............................ 544/215

Primary Examiner—John M. Ford
Attorney, Agent, or Firm—Anthony T. Lane; Edward Goldberg; Edward Costigan

[57] ABSTRACT

The invention provides a continuous moving bed reactor, useful for the preparation of 3,7-diacetyl-1,3,5,7-tetraazabicyclo-3.3.1-nonane (DAPT). The reactor makes novel use of water, a known catalyst for said reaction. However, in this invention, the water is present as ice. The ice is made to automatically promote and moderate the reaction as well as regulate the flow of hexamine into the reactor. These automatic functions are achieved by mixing ice with hexamine, the latter is one of two principle reactants used, to generate a standing bed of slurry. When melted at its base, the slurry advanced under the influence of gravity. The melting of the ice being caused by local application of the second principle reactant, acetic anhydride, which is a liquid.

The apparatus is constructed in the following way. A tube shaped reservoir for containing the cited slurry is open at the top end and terminates at its bottom end by a porous compartment. The latter compartment openly retains the slurry. A fluid delivery device, i.e. a nozzle, is contained within the porous compartment. The functions of the nozzle is to deliver acetic anhydrid to the hexamine contained in said slurry.

The porous compartment is contained within a larger nonporous vessel. The vessel is equipped with a stirrer, an ammonia inlet and a temperature sensing device. This vessel functions as a secondary reaction zone, in which more hexamine, and hece more DAPT, is prepared by an in-situ mechanism commonly known as resynthesis.

1 Claim, 1 Drawing Sheet

NONANE

This application is a division of application Ser. No. 07/687,607, filed Apr. 15, 1991.

FIELD OF USE

This invention relates to an improved reactor for use in making a percursor to HMX, and a method of making said precursor.

BACKGROUND OF THE INVENTION

The invention is concerned with a continuous, moving bed, reactor, useful in the preparation of 3,7-diacetyl-1,3,5,7-tetrazabicyclo-3,3,1-nonane (DAPT). DAPT is a chemical intermediate used in the production of the worlds most powerful military explosive HMX. DAPT is, therefore, a very important compound. Better methods of producing it are being continuously sought by many of the worlds governments. Common to all synthetic approaches, which use the preferred starting materials hexamine, and acetic anhydride, is the need to remove the massive amount of heat generated by the synthetic process. This heat has been measured by serveral independent researchers, and found to be approximately 500 BTU's per pound of DAPT synthesized. A quantity of heat about 3 times greater than the energy given off during the detonation of an equal amount of HMX. For a given synthetic system, the rate of production of DAPT is largely a matter of the efficiency. In other words, how fast can the system remove the heat, which if accumulated could cause the decomposition of the product.

Thus, the overall rate limiting step is the rate at which heat can be transferred through the wall of the heat exchanger. This ultimately determines the yield of the reaction since this is the rate and yield controlling step, greater performance of the system would come from better cooling.

Capitalization, pollution control, safety and operating costs are all of major importance in a production system. If risks can be controlled through a faster and more economical cooling system. This would be of great commercial importance to industry.

SUMMARY OF INVENTION

In one embodiment of this invention the properties of water, in the form of ice, are used to catalyze, cool and control a continuous synthetic reaction which produces DAPT. The invention consists, in principle, of an automatically balanced thermodynamic system. The cited system being controlled by the heat generated upon the addition of acetic anhydride to hexamine. The first principle reactant, i.e. acetic anhydride, being directed at the base of a self supporting column of ice slurry, which has entrained a controlled quantity of hexamine. The resulting exothermic reaction melts the ice at the base, causing liquefaction of the entire reaction medium at that point. Provision is made for the resulting liquefied-product mixture to flow away from such base. Thus, the column of ice descends to a mixing region in a continuous manner. The rate is substantially determined by the rate of heat generation during the reaction. The rate of reaction is further dependent upon the rate of addition of the acetic anhydride.

In the practice of this invention, the hexamine and ice ratio are predetermined, and fixed by the uniformity of the mixture. In the reactor, this mixture feeds automatically, and the rate is a constantly dependent upon a set of independent reactor variables. These include the stir rate, the surface area of a screened compartment, and the degree to which the compartment is submerged, among other things. It should be noted that all of these are independent. However, when all are held constant, these all drop out of the overall equation. Thus, the rate of addition of acetic anhydride is the only variable of concern. It is important to note that when all other variables are held constant, the rate of addition of acetic anhydride must coincide with the rate of addition of hexamine.

The above basis is also complicated by the fact that the rate of addition of hexamine is, to some extent, dependent upon the rate of addition of acetic anhydride. It should be noted that this relationship is not linear. If no acetic anhydride flows through the system, no reaction will take place. As a result, no hexamine will descend into the reactor. On the other hand, an excessive rate of addition will exceed the rate at which the hexamine can react.

Fortunately there is a simple solution to the above cited problem. The proper flow rate of acetic anhydride can be determined; this is accomplished by measurement of the reactor temperature at the outlet of the reactor.

The maximum temperature for a given ratio of hexamine to ice is determined in advance. This is accomplished by mixing a small sample quantity of the exact amount of reactants in a Dewar flask, and measuring the final temperature. Once the maximum temperature is determined, a similar experiment is performed to determine the final temperature, when a 20% excess of acetic anhydride is present. A third temperature is also determined, this is the temperature increase resulting when the exact amount of ammonia is added to the reaction solution, which contains a 20% excess of acetic anhydride.

DETAILED DESCRIPTION OF THE PREFERRED EMBODIMENT

Figure 1:
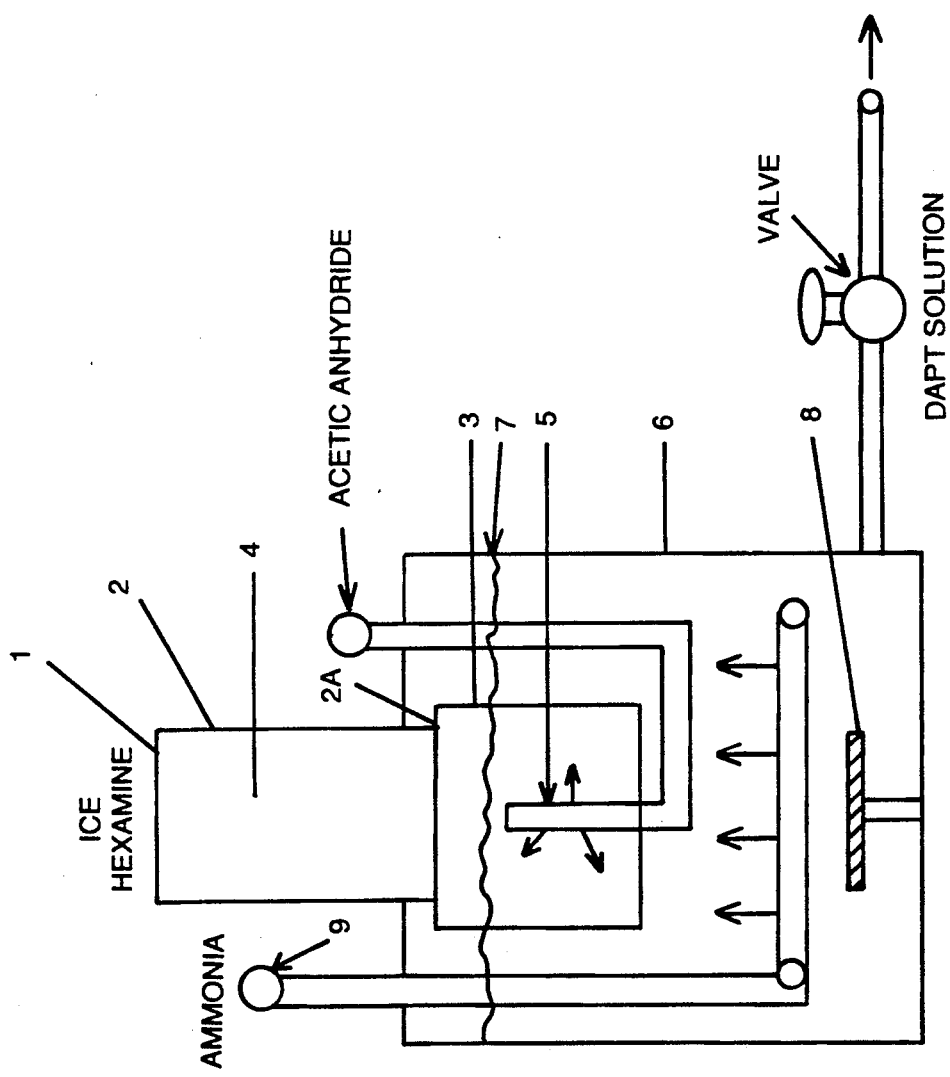

The ice performs a number of functions in the practice of this invention. Among these functions are catalysis, without which the reaction barely proceeds. And, also cooling of the reaction temperature generated. A ball mill, or other similar grinding and mixing device is used to prepare, either continuously or in batches, a supply or slurry composed of a calculated quantity of hexamine and ice. As shown in the FIGURE, the slurry is admitted at the top open end (1) of a vertical tube (2) which serves as a first reservoir. This reservoir terminated at its bottom end (2A) in a substantially smaller second reservoir or compartment (3). The compartment (3) may vary in shape, but must extend downwardly beyond the bottom of the said tube (2). The second reservoir or compartment (3) is constructed of wire mesh, screening, or other suitably like material. The size of the mesh or apertures of the screening material is of an operative size which will essentially prevent the gross outflow of the slurry (4) out of the second reservoir or compartment (3). The slurry is thus retained and supported within the confines of the combined areas of both reservoirs or compartments.

Additionally, a spray nozzle (5), or other similar fluid dispersing device, is permanently located within the second reservoir or compartment (3), as shown in the FIGURE. Different orientations and configurations of the said fluid dispersing device (5) are possible, but the function or structural configuration of the device must not restrict the slurry (4) from freely enveloping and surrounding it.

Thus, the compartment (3) functions as the first stage reaction zone of the reactor. The cited reaction zone is additionally enclosed within a nonporous container (6) which is at least several times the volume of the first reaction zone formed by compartment (3). The vertical tube (2), or first reservoir, projects vertically upward from the top of this enclosure (6).

During the operation of the reactor, as constructed, acetic anhydride is dispersed continuously from said fluid dispersing device (5), in a manner, so as to promote rapid mixing within the mass of said slurry (4). The mixing promoted by the dispersion of the acetic anhydride is limited to the slurry contained within the reaction zone (3). Such limiting of the rate of mixing is accomplished by control of the injection pressure and conventional nozzle design.

Acetic anhydride introlduced as described into the reactor zone, reacts on contact with the hexamine contained in said slurry. This resulting reaction is catalyzed by the ice. The result is an extremely rapid formation of DAPT, plus the normal by-products formaldehyde and acetic acid.

The reaction between the acetic anhydride and hexamine is by its nature very exothermic. In the prior art, the temperature must be moderated, or the reaction will overheat. If the latter happens to occur, only poor yields and unwanted side product will result. In the past the moderation or cooling of the reaction was accomplished by use of heat exchangers, high speed agitators, extended mechanical devices. This was accompanied by the slow addition of the reactants, or the addition of the both reactants in diluted form.

The above cited methods created a need to recycle the reactants, and this slowed, complicated, and added to the cost of the process.

In the practice of this invention, the released energy instantly melted the ice slurry (4), and the temperature was and is completely controlled. This eliminated the need for any moderators or moderating techniques.

This invention permits the cited reaction to be quantitatively performed at great speed. Control of the reaction by such means is so instantaneous that, when the quantity of ice in the hexamine slurry (4) is great enough, there is no measurable increase in temperature. Thus, said reaction can be made to take place in an isothermal way.

In practice, any desired operating temperature from 18 degrees below zero centigrade to the maximum for the cited reaction of 120 degrees above zero centigrade can be obtained, and this is accomplished simply by controlling the ice to hexamine ratio.

Further, and inherently, the melting of said ice (4) dissolves all the product, and all of the by-products, resulting in a continuous solution (7). The solution produced passes, easily and continuously, through the porous walls of the said compartment (3) and into the larger nonporous container (6).

Still further, the melting of the ice inherently provides a continuous supply of hexamine into said reaction zone (3). As the column of slurry within the tube, which contains both ice and hexamine, continuously descends under the influence of gravity, the reaction proceeds. This action automatically keeps the mesh compartment (3) filled, and the nozzle (5) completely engulfed with the mesh compartment (3) filled, and the nozzle (5) completely engulfed with the mixture of fresh hexamine and ice.

The reactant liquor (7) remains retained within the larger vessel. This is accomplished in such a quantity in order to maintain said mesh compartment substantially submerged, and beneath the level of said solution. This level, i.e. the level of the solution, is completely adjustable, and is used to control the overall rate of output of the reactor.

The described control is accomplished by the following procedure. The retained product solution (7) is continuously stirred. This promotes still further chemical and thermal interaction between the product solution and the mixture in the mesh compartment (3). The action of stirring (8) promotes a still further reaction by forming a secondary reaction zone (6), and further provides greater cooling to the second zone. Due to the heat of reaction, more ice melts, and this causes more hexamine to enter the aforesaid cited primary reaction zone (3). This zone is defined by the nozzle (5) and the screened compartment (3), and, as a result, regulates the rate at which acetic anhydride can be utilized. The rate of operation in the present case is proportional to the reactors residence time.

Ammonia (9) is admitted to the cited secondary zone by either bubbling in as a gas, or injected as a liquid. The ammonia (9) reacts with the byproduct, viz: formaldehyde, forming more hexamine in situ. The latter hexamine instantly reacts with the excess acetic anhydride, initially present, and forms additional DAPT. The product solution (7) is continuously drawn off to maintain the proper level of solution within the reactor.

In practice the reactor may be started and operated as in the following sequence.

CONTINUOUS REACTOR START UP

1. Charge hexamine/ice into the cited tube;
2. Establish stir rate;
3. Start acetic anhydride flow into the primary reaction zone or compartment.
4. Let secondary reaction zone or enclosure, fill to operating level, with the desired product and the excess of acetic anhydride.
5. Let temperature reach maximum;
6. Increase acetic anhydride flow to the primary zone or compartment. This can be to even a 20% excess as indicated by temperature drop;
7. Then, start, and increase ammonia flow until temperature rise indicates the proper flow rate of the desired product out of the system.

The liquidified product, which escapes from the primary reaction zone is retained in sufficient quantity in the compartment to maintain the primary zone in a substantially submerged condition as shown in the FIGURE. This mode of operation permits an acceleration of the reactors activity by promoting further heat transfer. Thus, faster melting of the ice brings hexamine into the system more rapidly. When a 20% excess of acetic anhydride is introduced within the primary reaction zone or compartment, and a sufficient quantity of ammonia is injected within the secondary zone or enclosure, a phenomenon termed resynthesis occurs.

The said phenomenon refers to the generation of additionaly hexamine, from the byproduct formaldehyde form in the first reaction zone or compartment and flow into the enclosure. The in-situ formation of hexamine in the second reaction zone or enclosure reacts with the excess acetic anhydride, initially injected within the primary reaction zone but which flowed out of the compartment, giving rise to a yield of 120% of the end product desired. This yield is based upon the initial quantity of hexamine employed.

In another embodiment of this invention, a semi-continuous process is demonstrated. A suitable container is provided with a stirrer. The enclosure or container with the cited stirrer is charged with a calculated quantity of ice and hexamine. The mixture is set stirring in the enclosure, and the required quantity of acetic anhydride is quickly added. The stirring is continued until all of the ice has melted, and the temperature has risen to the value desired. After this initial reaction is completed, ammonia as a gas, liquid, or salt such as ammonium acetate, is added to the mixture in the enclosure or container. The said mixture is stirred until the desired temperature is achieved and the reaction is again otherwise complete. At this point a valve located at the base of the container is opened, and the solution of product and byproducts flows into a second container (not shown). The second container acting as a reservoir from which a continuous supply of the product liquor emerges. The first process is again repeated, while maintaining the reservoir in a substantially filled condition. The liquor product desired being useful for the production of HMX as feedstock.

In the alternative, the desired product or feedstock can be dried to a solid for longer term storage.

A further embodiment of this invention demonstrates a simple batch process. The process being particularly useful, and convenient for the preparation of small quantities such as are used in a laboratory experiment.

It should be noted that different orientations and configurations of the said fluid dispersing device (5) are possible, but the latter device must not restrict the slurry (4) from freely enveloping and surrounding itself (5). As described, the compartment functions as the first stage reaction zone for the reactor. This reaction zone is additionally enclosed, as shown in the FIGURE, within a nonporous container or enclosure (6), the latter is typically several times the volume of the described reaction zone or compartment (3). The vertical tube (2) or reservoir projects vertically from the top of this enclosure or container (6). During operation of the reactor, acetic anhydride in about a 20% excess of that need for the reaction, is dispersed continuously from the fluid dispersing device, (5). This is to promote rapid mixing within the mass of the slurry (4). The Mixing is intentionally limited to the slurry contained within the reaction zone (3). Limiting of the action of mixing is accomplished by control of the injection pressure and nozzle design of the injection tube (5). Acetic anhydride introduced, as described, reacts on contact with the hexamine contained in said slurry, and this reaction is catalyzed by the ice, resulting in an extremely rapid formation of DAPT and the normal by-products formaldehyde and acetic acid.

ADVANTAGES OF PRESENT INVENTION

The invention herein described offers these advantages as well as others in the following ways. The heat energy produced is taken up instantly by the melting of ice, and this is present throughout the reaction medium. The presence of water in the reaction, catalyzes and causes the reaction to be carried out, as fast as the reactants can be mixed. The reactor is not merely a space where the reactants are mixed at high speed. As should be noted, in accordance with the present invention, the hexamine slurry is made to enter the reaction zone as a direct result of the melting of the ice. This melting of the ice being caused by the reaction itself. The rate of the hexamine flow into the reactor is directly dependent thermodynamically on the rate of reaction.

The foregoing disclosure and drawings are merely illustrative of the principle of this inventions and are not to be interpreted in a limiting sense. We wish it to be understood that we do not desire to be limited to the exact details of construction shown and described because obvious modifications will occur to a person skilled in the art.

It is claimed that:

1. In the improved process of making 3,7-diacetyl-1,3,5,7-tetraaza bicyclo-3,3,1-nonane wherein an exotherm is a rate limiting factor, the improvement comprising absorbing said exotherm by a change of phase from the frozen solid state to a liquid state of common ice.

* * * * *